US012268582B2

(12) United States Patent
Chatterjee et al.

(10) Patent No.: US 12,268,582 B2
(45) Date of Patent: *Apr. 8, 2025

(54) ABSORBENT ARTICLE HAVING WAIST GASKETING ELEMENT

(71) Applicant: The Procter & Gamble Company, Cincinnati, OH (US)

(72) Inventors: Kumardipti Chatterjee, Indian Hill, OH (US); Tina Brown, Cincinnati, OH (US); Joseph Hung Lam, Mason, OH (US); Miguel Caballero, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/605,981

(22) Filed: Mar. 15, 2024

(65) Prior Publication Data
US 2024/0216187 A1    Jul. 4, 2024

Related U.S. Application Data

(63) Continuation of application No. 17/396,917, filed on Aug. 9, 2021, now Pat. No. 11,963,855, which is a
(Continued)

(51) Int. Cl.
A61F 13/49       (2006.01)
A61F 13/15       (2006.01)
(Continued)

(52) U.S. Cl.
CPC .... A61F 13/4902 (2013.01); A61F 13/15203 (2013.01); A61F 13/15723 (2013.01);
(Continued)

(58) Field of Classification Search
CPC ........ A61F 13/15; A61F 13/49; A61F 13/513; A61F 13/514; A61F 13/475;
(Continued)

(56) References Cited

U.S. PATENT DOCUMENTS 4,753,646 A    6/1988 Enloe
5,151,092 A    9/1992 Buell
(Continued)

FOREIGN PATENT DOCUMENTS

EP    1621168 A1    2/2006
EP    2595592 B1    11/2014
(Continued)

OTHER PUBLICATIONS

All Office Actions, U.S. Appl. No. 15/599,700 filed on May 19, 2017.
(Continued)

Primary Examiner — Michele Kidwell
(74) Attorney, Agent, or Firm — Charles R. Matson

(57) ABSTRACT

An absorbent article for wearing about the lower torso of a wearer includes a waist gasketing element disposed in one of the first or the second waist regions and joined to the chassis in a chassis attachment region. The waist gasketing element comprises an outboard lateral edge and an inboard lateral edge. The chassis attachment region comprises a first zone proximate to the outboard lateral edge and a second zone disposed longitudinally inboard of the first zone. Each of the first and the second zones comprise one or more chassis attachment bonds. The first zone comprises a first total basis weight and the second zone comprises a second total basis weight, wherein the second total basis weight is greater than the first total basis weight.

18 Claims, 7 Drawing Sheets

Related U.S. Application Data continuation of application No. 15/599,700, filed on May 19, 2017, now Pat. No. 11,129,757.

(60) Provisional application No. 62/339,248, filed on May 20, 2016.

(51) Int. Cl.
  *A61F 13/513* (2006.01)
  *A61F 13/514* (2006.01)

(52) U.S. Cl.
  CPC .................. *A61F 13/15756* (2013.01); *A61F 13/49012* (2013.01); *A61F 13/49019* (2013.01); *A61F 13/49061* (2013.01); *A61F 13/15* (2013.01); *A61F 2013/1513* (2013.01); *A61F 2013/15146* (2013.01); *A61F 13/49* (2013.01); *A61F 2013/49022* (2013.01); *A61F 2013/49092* (2013.01); *A61F 2013/49093* (2013.01); *A61F 13/51305* (2013.01); *A61F 13/51394* (2013.01); *A61F 13/514* (2013.01)

(58) Field of Classification Search
  CPC .............. A61F 13/4751; A61F 13/4752; A61F 13/4755; A61F 13/4756; A61F 13/4757; A61F 13/494
  See application file for complete search history.

(56) References Cited

U.S. PATENT DOCUMENTS

| | | |
|---|---|---|
| 5,397,318 A | 3/1995 | Dreier |
| 5,514,121 A | 5/1996 | Roe et al. |
| 5,827,259 A | 10/1998 | Laux |
| 5,904,675 A | 5/1999 | Laux |
| 5,938,652 A | 8/1999 | Sauer |
| 5,993,433 A | 11/1999 | St. Louis |
| 6,018,093 A | 1/2000 | Roe et al. |
| 6,280,426 B1 | 8/2001 | Turner et al. |
| 7,879,017 B1 | 2/2011 | Tabata |
| 8,372,053 B2 | 2/2013 | Shimada et al. |
| 9,023,007 B2 | 5/2015 | Hashino |
| 10,123,914 B2 | 11/2018 | Kobayashi et al. |
| 11,129,757 B2 | 9/2021 | Chatterjee et al. |
| 11,963,855 B2 * | 4/2024 | Chatterjee ......... A61F 13/49061 |
| 2004/0122413 A1 | 6/2004 | Roessler |
| 2004/0243085 A1 | 12/2004 | Veith |
| 2006/0058767 A1 | 3/2006 | Zhang et al. |
| 2008/0051755 A1 | 2/2008 | Otsubo |
| 2011/0046589 A1 | 2/2011 | Kawakami et al. |
| 2012/0277703 A1 | 11/2012 | Rhein |
| 2014/0000795 A1 | 1/2014 | Hamilton |
| 2016/0106601 A1 | 4/2016 | Kobayashi |
| 2017/0000661 A1 | 1/2017 | Chatterjee et al. |
| 2017/0239104 A1 | 8/2017 | Jang et al. |
| 2017/0246055 A1 | 8/2017 | Barnes |
| 2017/0333261 A1 | 11/2017 | Chatterjee |
| 2021/0369507 A1 | 12/2021 | Chatterjee et al. |

FOREIGN PATENT DOCUMENTS

| | | |
|---|---|---|
| JP | H11137601 A | 5/1999 |
| JP | 2000107223 A | 4/2000 |
| JP | 2004229857 A | 8/2004 |
| JP | 2008136793 A | 6/2008 |
| WO | 200007534 A1 | 2/2000 |
| WO | 2007037390 A1 | 4/2007 |
| WO | 2012073901 A1 | 6/2012 |
| WO | 2016068963 A1 | 5/2016 |

OTHER PUBLICATIONS

All Office Actions; U.S. Appl. No. 17/396,917, filed on Aug. 9, 2021.

International Search Report and Written Opinion; Application Ser. No. PCT/US2017/033534; dated Jul. 19, 2017; 13 pages.

* cited by examiner

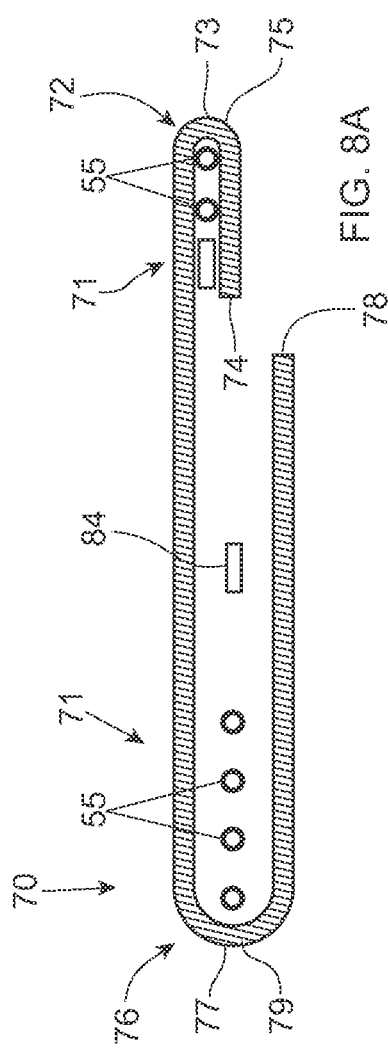
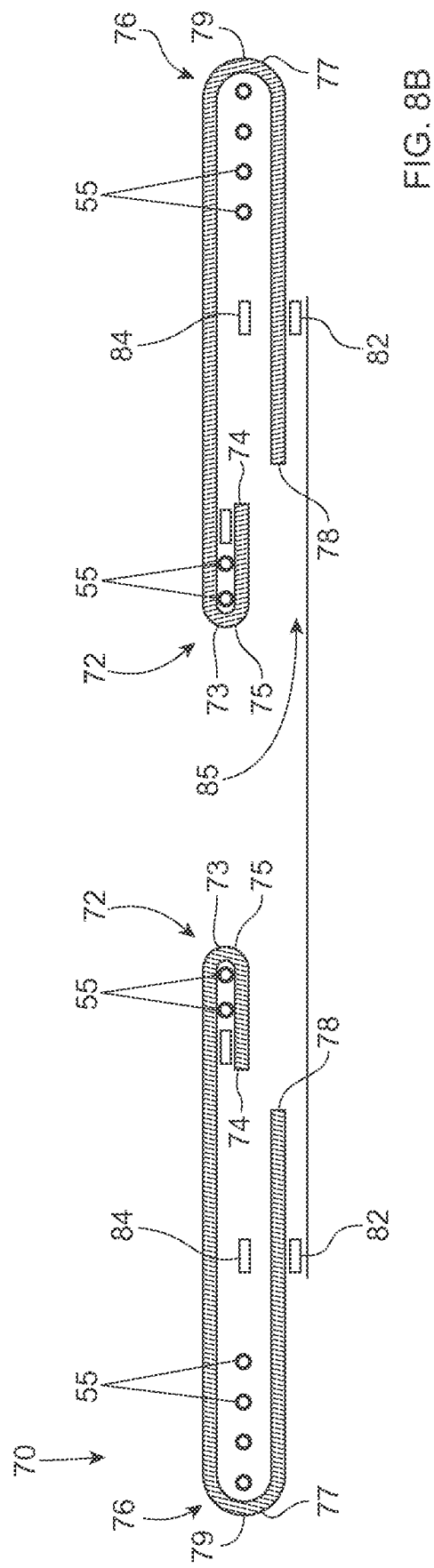

ABSORBENT ARTICLE HAVING WAIST GASKETING ELEMENT

CROSS REFERENCE TO RELATED APPLICATIONS

This application claims priority under 35 U.S.C. § 120 and is a continuation of U.S. patent application Ser. No. 17/396,917, filed on Aug. 9, 2021, which is a continuation of U.S. patent application Ser. No. 15/599,700, filed on May 19, 2017, which claims priority under 35 U.S.C. § 119(e) to U.S. Provisional Patent Application Ser. No. 62/339,248, filed on May 20, 2016, the entire disclosures of all of which are hereby fully incorporated by reference herein.

FIELD OF THE INVENTION

This invention relates to absorbent articles (e.g., diapers, adult incontinence articles) having waist gasketing elements.

BACKGROUND OF THE INVENTION

It has long been known that absorbent articles such as conventional absorbent articles (e.g., diapers, adult incontinence articles, feminine hygiene pads) offer the benefit of receiving and containing urine and/or other bodily exudates (e.g., feces, menses, mixture of feces and urine, mixture of menses and urine, etc.). To effectively contain bodily exudates, the article should provide a snug fit around the waist and legs of a wearer.

Manufacturers often use elasticized areas, such as elasticized waistbands, within the article to help achieve a snug fit. Elasticized waistbands are often discrete components joined to other components of an absorbent article (i.e., the chassis) by one or more bonds. In order to ensure the waistband remains attached, the attachment bonds must be sufficiently strong. However, the strength of attachment bonds often counteracts other desirable properties such as surface softness and smooth edges, particularly where the waistband edge contacts the wearer's skin. Indeed, higher amounts of bonding material, larger bonds, and/or a higher number of bonds can create rough edges and surfaces on the waistband. Moreover, when adhesive is the bonding material, said adhesive may become exposed during manufacturing and/or handling and consequently may come into contact with the end user.

Therefore, there is a need for an article having an attached waistband where there is a more effective balance of bonding strength with desirable tactile and/or safety properties. There is also a need for an article having a waistband that has a high quality garment-like appearance. Further, there is a need for a cost efficient and effective process for manufacturing articles with elasticized waistbands.

SUMMARY OF THE INVENTION

An absorbent article for wearing about the lower torso of a wearer includes a first waist region having a first waist edge, a second waist region having a second waist edge, and a crotch region disposed between the first and second waist regions. The article further includes a first longitudinal edge and a second longitudinal edge; and a chassis comprising a topsheet, a backsheet, and an absorbent core disposed between the topsheet and backsheet. A waist gasketing element, having an inboard lateral edge and an outboard lateral edge, is disposed in one of the first or the second waist regions and joined to the chassis in a chassis attachment region.

The chassis attachment region comprises a first zone proximate to the outboard lateral edge and a second zone at least partially disposed longitudinally inboard of the first zone. Each of the first and the second zones comprise one or more chassis attachment bonds.

The first zone comprises a first aggregate bond area and the second zone comprises a second aggregate bond area, and the second aggregate bond area may be greater than the first aggregate bond area. Additionally or alternatively, the first zone comprises a first aggregate bond strength and the second zone comprises a second aggregate bond strength, wherein the second aggregate bond strength is greater than the first aggregate bond strength. Additionally or alternatively still, the first zone comprises a first total basis weight and the second zone comprises a second total basis weight, wherein the second total basis weight is greater than the first total basis weight.

Methods for creating articles comprising waist gasketing elements are also disclosed.

BRIEF DESCRIPTION OF THE DRAWINGS

FIGS. 8a-8b are schematic cross-sectional views of an exemplary embodiment of the leg gasketing systems and topsheet of FIG. 1, the cross section taken along the lateral centerline. The leg gasketing systems are shown in a flat, uncontracted state.

DETAILED DESCRIPTION OF THE INVENTION

Definitions

Figure 1:
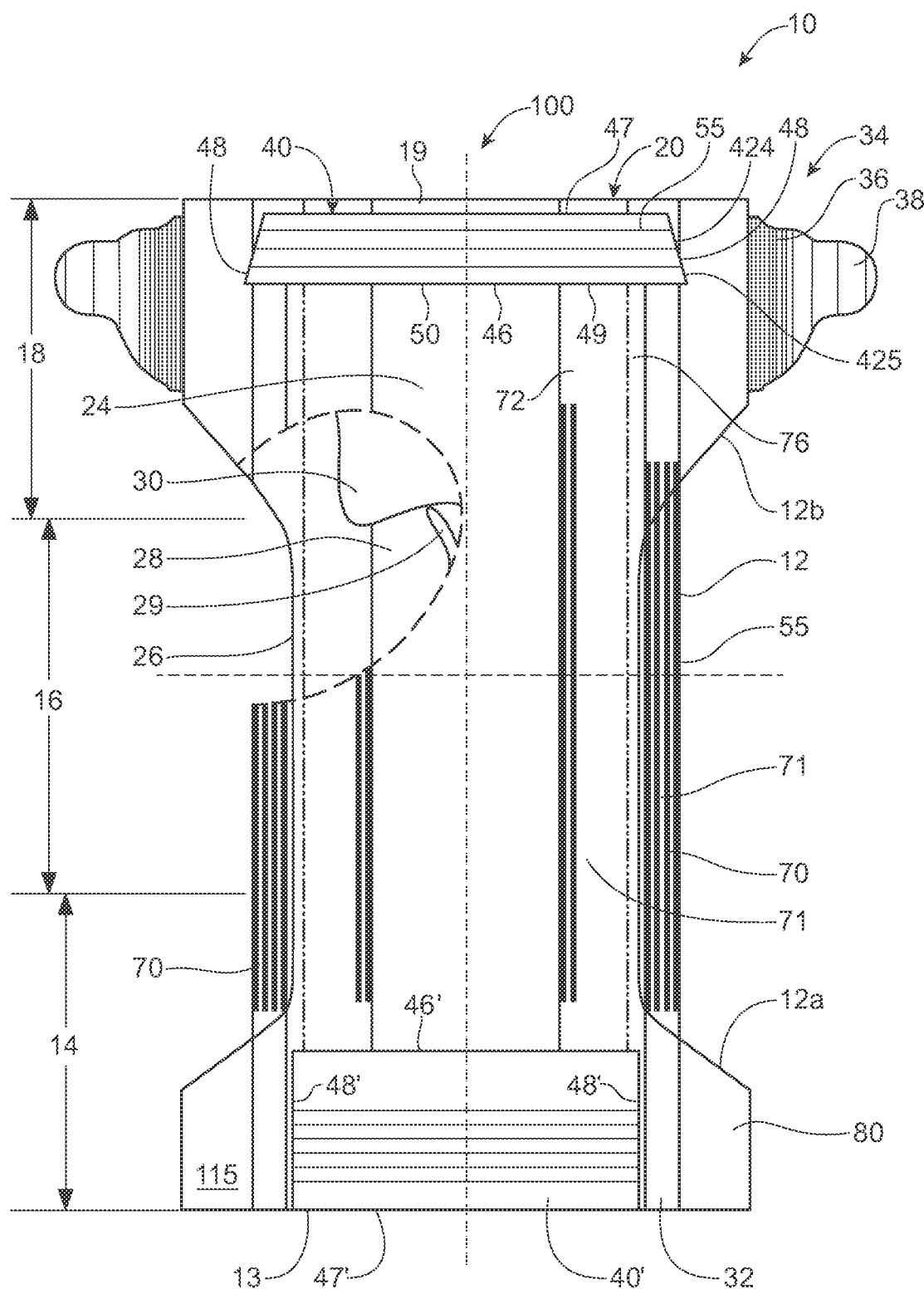
FIG. 1 is a schematic plan view of an exemplary embodiment of an absorbent article as detailed herein. The absorbent article is shown in a flat, uncontracted state.

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Bonding technique" refers to the manner in which a bond is formed, including but not limited to bonding material and/or method (e.g., adhesive, ultrasonic, heat etc.), intermittency or continuity within bonding regions, bond shape, bond size, and bond area or aggregate bond area. Bonding techniques include adhesive bonding, mechanical bonding, pressure bonding, ultrasonic bonding, heat bonding and workable combinations thereof. Suitable bonding techniques may additionally include continuous or intermittent bonding, a random assortment bond sites, or any workable combination thereof.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal." Longitudinal distances are measured between points disposed along a longitudinal line.

"Lateral" refers to a direction running from a longitudinal edge to an opposing longitudinal edge of the article and generally at a right angle to the longitudinal direction. Directions within 45 degrees of the lateral direction are considered to be "lateral." Lateral distances are measured between points disposed along a lateral line.

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor (i.e., may be "vapor-permeable").

"Elongatable," "extensible," or "stretchable" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery). Elastomeric materials may include elastomeric films (including but not limited to films derived from rubber and/or other polymeric materials), polyurethane films, elastomeric foams, scrims, elastic nonwovens, synthetic fibers such as LYCRA® and other sheet-like structures. An elastic member comprises elastomeric material. Elasticized means that the component comprises elastomeric material.

"Proximate" as used herein means within 4 mm (i.e., a distance between proximate element is 4 mm or less).

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

Absorbent Article

FIG. 1 is a plan view of an exemplary, non-limiting embodiment of an absorbent article 10 of the present invention in a flat, uncontracted state. The body-facing surface 115 of the absorbent article 10 is facing the viewer. The absorbent article 10 includes a longitudinal centerline 100 and a lateral centerline 110.

The absorbent article 10 comprises a chassis 20. The absorbent article 10 and chassis 20 are shown to have a first waist region 14, a second waist region 18 opposed to the first waist region 14, and a crotch region 16 located between the first waist region 14 and the second waist region 18. The waist regions 14 and 18 generally comprise those portions of the absorbent article 10 which, when worn, encircle the waist of the wearer. The waist regions 14 and 18 may include elastic members 55 such that they gather about the waist of the wearer to provide improved fit and containment. The crotch region 16 is the portion of the absorbent article 10 which, when the absorbent article 10 is worn, is generally positioned between the legs of the wearer.

The outer periphery of the chassis 20 is defined by longitudinal edges 12 and waist edges (first waist edge 13 in first waist region 14 and second waist edge 19 in second waist region 18). The longitudinal edges 12 may be subdivided into a front longitudinal edge 12a, which is the portion of the longitudinal edge 12 in the first waist region 14, and a rear longitudinal edge 12b, which is the portion of the longitudinal edge 12 in the second (rear) waist region 18. The chassis 20 may have opposing longitudinal edges 12 that are oriented generally parallel to the longitudinal centerline 100. However, for better fit, longitudinal edges 12 may be curved or angled to produce, for example, an "hourglass" shape article when viewed in a plan view as shown in FIG. 1. The chassis 20 may have opposing lateral edges 13, 19 (i.e., the first waist edge 13 and second waist edge 19) that are oriented generally parallel to the lateral centerline 110.

The chassis 20 may comprise a liquid permeable topsheet 24, a backsheet 26, and an absorbent core 28 between the topsheet 24 and the backsheet 26. In embodiments that include one or more opacity strengthening patches 80, the chassis 20 also comprises the opacity strengthening patch(es) 80. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In some embodiments, an acquisition-distribution system 30 is disposed between the topsheet 26 and the absorbent core 28.

In certain embodiments, the chassis 20 comprises the main structure of the absorbent article 10 with other features added to form the composite absorbent article structure. While the topsheet 24, the backsheet 26, and the absorbent core 28 may be assembled in a variety of well-known configurations, absorbent article configurations are described generally in U.S. Pat. Nos. 3,860,003; 5,151,092; 5,221,274; 5,554,145; 5,569,234; 5,580,411; and 6,004,306.

Topsheet

The topsheet 24 is generally a portion of the absorbent article 10 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. One topsheet 24 useful herein is available from BBA Fiberweb, Brentwood, TN as supplier code 055SLPV09U. The topsheet 24 may be apertured.

Any portion of the topsheet 24 may be coated with a lotion or skin care composition as is known in the art. Non-limiting examples of suitable lotions include those described in U.S. Pat. Nos. 5,607,760; 5,609,587; 5,635,191; and 5,643,588. The specific examples are not limiting, as any lotion or skin care composition known in the art may be utilized. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

Absorbent Core

The absorbent core 28 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In some embodiments, the absorbent core may comprise one or more channels 29, wherein said channels are substantially free of absorbent particulate polymer material. The channels 29 may extend longitudinally or laterally. The absorbent core may further comprise two or more channels. In one nonlimiting example, two channels are symmetrically disposed about the longitudinal axis.

Exemplary absorbent structures for use as the absorbent core 28 are described in U.S. Pat. No. 4,610,678; 4,673,402; 4,834,735; 4,888,231; 5,137,537; 5,147,345; 5,342,338; 5,260,345; 5,387,207; 5,397,316, and U.S. patents application Ser. Nos. 13/491,642 and 62/210,100.

Backsheet

The backsheet 26 is generally positioned such that it may be at least a portion of the garment-facing surface of the absorbent article 10. Backsheet 26 may be designed to prevent the exudates absorbed by and contained within the absorbent article 10 from soiling articles that may contact the absorbent article 10, such as bed sheets and undergarments. In certain embodiments, the backsheet 26 is substantially water-impermeable. Suitable backsheet 26 materials include films such as those manufactured by Tredegar Industries Inc. of Terre Haute, IN and sold under the trade names X15306, X10962, and X10964. Other suitable backsheet 26 materials may include breathable materials that permit vapors to escape from the absorbent article 10 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, TX, under the designation EXXAIRE. Suitable breathable composite materials comprising polymer blends are available from Clopay Corporation, Cincinnati, OH under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer. The backsheet 26 may comprise an outer cover and an inner layer. The outer cover may be made of a soft, non-woven material. The inner layer may be made of a substantially liquid-impermeable film, such as a polymeric film. The outer cover and an inner layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

Ears/Fasteners

The absorbent article 10 may include front ears 32 and/or back ears 34. The ears 32, 34 may be integral with the chassis or discrete elements joined to the chassis 20. The ears 32, 34 may be extensible, inextensible, elastic, or inelastic. The ears 32, 34 may be formed from nonwoven webs, woven webs, knitted fabrics, polymeric and elastomeric films, apertured films, sponges, foams, scrims, and combinations and laminates thereof. In some embodiments, the ear 32, 34 may include elastomers (e.g., elastic strands, LYCRA® fibers), such that the ear is stretchable. In certain embodiments, the ears 32, 34 may be formed of a stretch laminate such as a nonwoven/elastomeric material laminate or a nonwoven/elastomeric material/nonwoven laminate, which also results in the ear being stretchable. Stretch laminates may be formed by any method known in the art. For example, the ears 32, 34 may be formed as a zero strain stretch laminate, which includes at least a layer of nonwoven material and an elastomeric element. The zero strain activation processes is disclosed, for example, in U.S. Pat. Nos. 5,167,897 and 5,156,793.

The absorbent article 10 may also include a fastening system 36. When fastened, the fastening system 36 interconnects the first waist region 16 and the rear waist region 18 resulting in a waist circumference that may encircle the wearer during wear of the absorbent article 10. The fastening system 36 may comprise a fastener 38 such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. In some embodiments, the fastening system 36 and/or the fastener 38 is foldable.

The fastening system 36 may be joined to any suitable portion of the article 10 by any suitable means. In some embodiments, the fastening system is joined to the ear 32, 34. In one nonlimiting example, the fastening system 36 and/or the fastener 38 is mechanically bonded to the ear 32, 34.

Waist Gasketing Element

The disposable absorbent article 10 may include at least one waist gasketing element 40 attached to the chassis 20. The waist gasketing element 40 may be disposed on the body facing side 115 of the chassis or a body-facing side of a layer of the chassis 20. In certain embodiments, the waist gasketing element 40 is joined to the topsheet 24 and/or to a leg gasketing system 70 as shown in FIG. 1. In other embodiments, the waist gasketing element 40 may be disposed on the garment-facing side 120 of the article or a garment-facing side of a layer of the chassis. For example, the waist gasketing element may be joined to the backsheet 26. Alternatively, the waist gasketing element may be disposed between the topsheet 24 and the backsheet 26.

Figure 2:
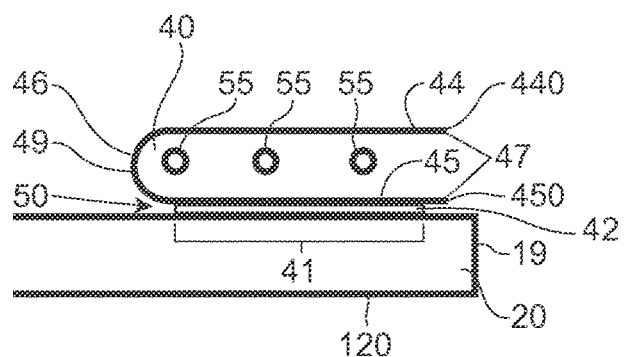
FIG. 2 is a schematic cross sectional view of the waist gasketing element disposed in the second waist region of FIG. 1.

In an embodiment, the waist gasketing element 40 comprises an elasticized waistband comprising one or more elastic members 55 as shown in FIG. 1. Waist gasketing elements 40 may be joined to the chassis 20 in the first waist region 14 and/or in the second waist region 18. In one nonlimiting example, the waist gasketing element 40 is disposed in the second waist region 18. Waist gasketing elements 40 may be joined to the chassis 20 in a chassis attachment region 41 by one or more chassis attachment bonds 42 as shown in FIG. 2 for example. (FIG. 2 is a schematic cross sectional view of the waist gasketing element disposed in the second waist region of FIG. 1. The waist gasketing element is shown in a non-compressed manner for ease of understanding.) The chassis bond(s) 42 may be formed by any suitable bonding technique, including but not limited to adhesive bonding, mechanical bonding, pressure bonding, ultrasonic bonding, heat bonding and combinations thereof. In one nonlimiting example, a chassis bond 42 is an adhesive bond.

The waist gasketing element 40 comprises a top layer 44 and a bottom layer 45. The top layer and/or the bottom layer may comprise a nonwoven, a film, a laminate of nonwovens and/or films, or combinations thereof. In one embodiment, the waist gasketing element 40 comprises a single, continuous web of material and therefore the top and bottom layers 44, 45 are integral and may be formed by folding the single, continuous web. In other embodiments, the waist gasketing element(s) 40 may be formed from more than one web of material (e.g., multiple webs of material that are joined together to become one web of material, or multiple distinct webs of material that are separate from the disposable absorbent article chassis and form part of the waist gasketing element). In such embodiments, the top layer 44 may be a formed form a different web of material than that of the bottom layer 45. The component materials in the distinct webs may be the same or they may be different. In some embodiments, neither the top layer nor the bottom layer is integral with the chassis (i.e., the waist gasketing element is discrete from the chassis).

Herein, locations (e.g., folded edge, material edge, etc.) on the waist gasketing element 40 are detailed in reference to "a web of material", "a portion of the web of material" or "waist gasketing material." The recitations of "a web of material" or "the web of material" or "waist gasketing material" refer to waist gasketing element embodiments that may be formed from a single, continuous web of material, multiple webs of material that are joined together to become one web of material, a single material that is folded to form multiple layers of the same material, a single material that is slit apart and rejoined together, or multiple distinct webs of material that may be separate from the disposable absorbent article chassis and form part of the waist gasketing element 40. All such embodiments are contemplated.

The waist gasketing element 40 includes an inboard lateral edge 46, an outboard lateral edge 47, and two longitudinal edges 48 as shown for example in FIGS. 1 and 2. The outboard lateral edge 47 may be coterminous with a waist edge 13, 19. Alternatively, the outboard lateral edge 47 may be disposed longitudinally inward of the waist edge 13, 19. The periphery of the waist gasketing element (e.g., the lateral and longitudinal edges) defines a waist gasketing element area, A1 (i.e., the mathematical, two-dimensional area of the waist gasketing element).

In further embodiments, the web of material forming the waist gasketing element 40 is folded longitudinally outward (away from the lateral centerline 110 of the absorbent article 10) to form the inboard lateral edge 46. In such embodiments, the inboard lateral edge 46 comprises a folded edge 49 and the outboard lateral edge 47 comprises a first material edge 440, which may be the material edge of the top layer 44 and a second material edge 450 which may comprise the material edge of the bottom layer 45. Although an embodiment depicting a waist gasketing element 40 with one folded edge 49 and two material edges 440, 450 is shown in FIG. 2, alternate constructions of useful waist gasketing elements are contemplated. For example, an alternate waist gasketing element 40 may include two distinct webs of material and therefore have four material edges (two on the inboard lateral edge 46, and two on the outboard lateral edge 47 or said differently, two opposed edges on the top layer 44 and two opposed edges on the bottom layer 45). As another nonlimiting example, an alternate waist gasketing element 40 may have a continuous web material that is formed into having two folded edges (one on the inboard lateral edge 46, and one on the outboard lateral edge 47) and two longitudinal material edges.

In a further embodiment, the waist gasketing element 40 may be used in conjunction with a leg gasketing system 70 as shown in FIG. 1. In such embodiment, the waist gasketing element 40 is attached to: 1) the chassis 20 and 2) the leg gasketing system 70, such that at least a portion of the outboard lateral edge 47 of the waist gasketing element 40 is attached to the chassis 20 and at least a portion of the outboard lateral edge 47 of the waist gasketing element 40 is attached to the web of material of the leg gasketing system 70. The inboard lateral edge 46 of the waist gasketing element 40 may be unattached to the chassis 20 of the disposable absorbent article 10. In embodiments that include a waist gasketing element 40 that has a waist gasketing element folded edge 49, a waist gasketing element first material edge 440, and a waist gasketing element second material edge 450, at least a portion of the web of material between the waist gasketing element folded edge 49 and waist gasketing element second material edge 450 is attached to the topsheet 24 and/or backsheet 26 of the chassis 20.

Figure 3:
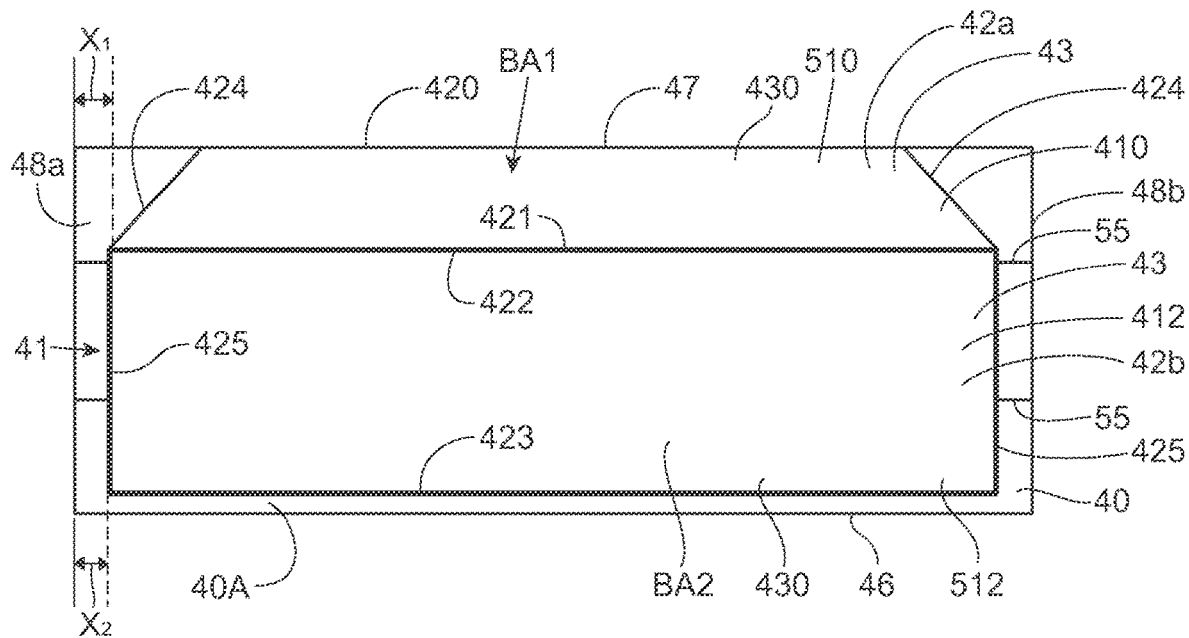
FIG. 3 is a schematic plan view of an exemplary embodiment of a waist gasketing element as detailed herein. The waist gasketing element is shown in a flat, uncontracted state.
Figure 4:
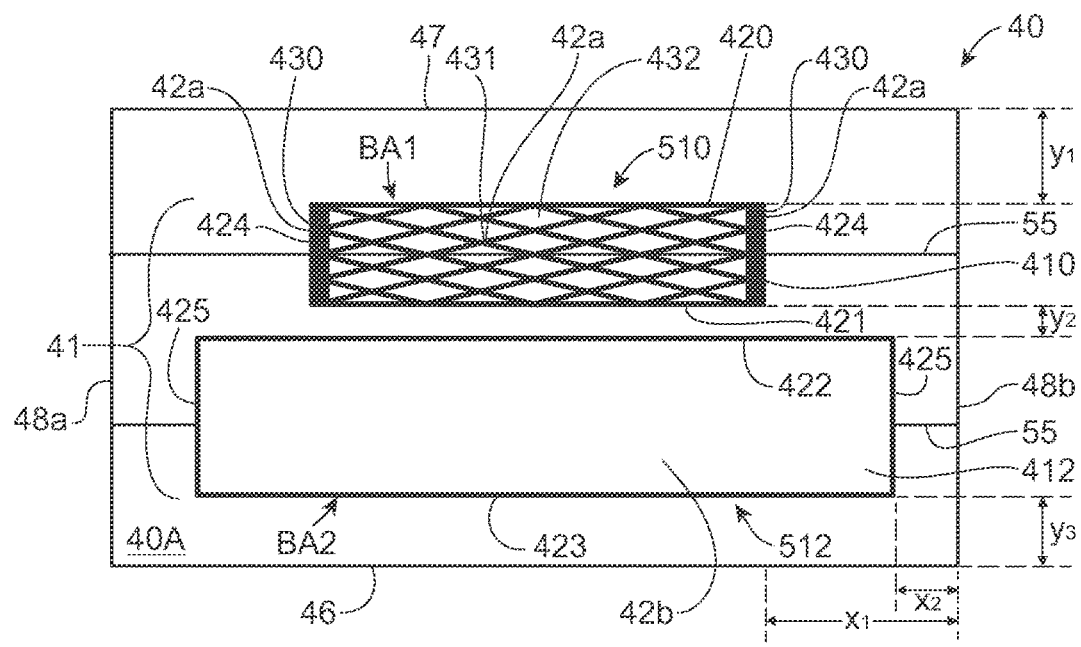
FIG. 4 is a schematic plan view of an exemplary embodiment of a waist gasketing element as detailed herein. The waist gasketing element is shown in a flat, uncontracted state.

The attachment of the waist gasketing element 40 to the chassis 20 is made through utilization of one or more chassis attachment bonds 42 disposed in a chassis attachment region 41. As shown in FIGS. 3 and 4, the chassis attachment region 41 may comprise a first zone 410 and a second zone 412. (FIGS. 3 and 4 are schematic plan views of a surface 40A of waist gasketing element that would be attached to the chassis and/or to the leg gasketing system.) The first zone may be disposed proximate to the outboard lateral edge 47. The second zone 412 may be disposed longitudinally inboard of the first zone, such that the second zone is at least partially between the first zone and the inboard lateral edge 46. Each zone may comprise one or more chassis attachment bonds 42. A chassis attachment bond may take the form of an adhesive bond, heat bond, pressure bond, mechanical bond, or any other bonding technique known in the art. In some embodiments, one or both zones comprise at least one adhesive chassis attachment bond 43.

The first zone 410 may be at least partially coextensive with the outboard lateral edge 47, such that at least one chassis attachment bond 42a in the first zone comprises an outboard bond edge 420 that is at least partially coextensive with the outboard lateral edge 47 as shown in FIG. 3. Alternatively, as shown in FIG. 4, the first zone may be spaced apart from the outboard edge 47 by a longitudinal distance $Y_1$, where $Y_1$ is the smallest longitudinal distance between an outboard bond edge 420 of a bond 42a in the first zone 410 and the outboard lateral edge 47. Said differently, where more than one bond is present in the first zone, $Y_1$ is the shortest longitudinal distance between (i) the bond 42a that is longitudinally closest to the outboard lateral edge 47 and (ii) said outboard lateral edge 47. In some embodiments, $Y_1$ is at least 2 mm, or at least 10 mm, or at least 20 mm, or at least 50 mm; or any range or distance within the range of about 2 mm to about 50 mm. In further embodiments, the outboard lateral edge 47 is at least partially coterminous with a waist edge. In such embodiments, $Y_1$ is also the distance between the first zone and the waist edge. Likewise, the first zone may be at least partially coextensive with a longitudinal edge 48a, 48b or set apart by a minimum distance $X_1$, where $X_1$ is the shortest lateral distance between a longitudinal bond edge 424 and a proximate longitudinal edge 48. The right side of the waist gasketing system may differ from the left side, such that the distances between edge bonds 424 and longitudinal edges on opposite sides of the waist gasketing system may be different.

The second zone 412 may be adjacent to the first zone 410 (i.e., at least one bond 42a in the first zone 410 has an inboard bond edge 421 that is at least partially coextensive with an outboard edge 422 of a bond 42b in the second zone) as shown in FIG. 3. Alternatively, the second zone may be spaced apart from the first zone by a longitudinal distance, $Y_2$, where $Y_2$ is the smallest longitudinal distance between an inboard bond edge 421 of a bond 42a in the first zone and an outboard edge 422 of a bond 42b in the second zone as shown in FIG. 4. Where more than one bond is present in the first zone and/or in the second zone, $Y_2$ is the shortest longitudinal distance between the two closest bonds 42a, 42b.

The second zone 412 may be at least partially coextensive with the inboard lateral edge 46, such that at least one chassis attachment bond 42b in the second zone comprises an inboard edge 423 that is at least partially coextensive with the inboard lateral edge 46 of the waist gasketing element. In some further embodiments, the second zone is spaced apart from the inboard lateral edge 46 by a longitudinal distance $Y_3$, where $Y_3$ is the smallest longitudinal distance between the inboard edge 423 of a bond 42b in the second zone and the inboard lateral edge 46 as shown in FIG. 4 for example. Where more than one bond is present in the second zone, $Y_3$ is the shortest longitudinal distance between (i) the bond 42b that is laterally closest to the inboard lateral edge 46 and (ii) said inboard lateral edge 46. In certain embodiments, $Y_3$ can be from about 0 mm to about 4 mm. Likewise, the second zone may be at least partially coextensive with a longitudinal edge 48 or set apart by a minimum distance $X_2$ from the longitudinal edge 48, where $X_2$ is the shortest lateral distance between a longitudinal bond edge 425 and a proximate longitudinal edge 48. The right side of the waist gasketing system may differ from the left side, such that the distances between edge bonds 425 and longitudinal edges on opposite sides of the waist gasketing system may be different. Further still, $X_2$ may differ from $X_1$ as shown in FIGS. 3-4.

The first zone 410 may comprise a first bonding technique 510, and the second zone 412 may comprise a second bonding technique 512. The first bonding technique may differ from the second bonding technique. In particular, the techniques may differ by the type of bonding material, the amount of bonding material, bonding method, number of bonds, and/or aggregate bond area.

The first zone and/or the second zone may comprise adhesive bond(s) 43. An adhesive bond 43 may be in the form of a substantially continuous bar 430 as shown for example in FIG. 3. In other embodiments, an adhesive bond 43 is in the form of a web-like structure 431 having one or more open areas 432 as depicted in FIG. 4. It is believed that the open areas (i.e., adhesive-free areas) allow for puckers in the waist gasketing material and/or chassis material and/or leg gasketing material, creating a soft, cushiony feel. Additionally or alternatively, a plurality of adhesive bonds 43 may be intermittently provided in the first and/or second zone, which may also provide a plurality of open areas 432. An exemplary adhesive useful in the present invention is N Adhesive Henkel DM3800 (720VP M1) F Dispomelt. An adhesive bond in the first zone and an adhesive bond in the second zone may be created by the same type of adhesive or by a different type of adhesive.

In some embodiments, the first zone 410 and the second zone 412 may comprise different bond areas. Each chassis attachment bond 42 comprises an individual bond area (i.e., the two dimensional, mathematical area of the bond). The first zone comprises a first aggregate bond area, BA1, which is sum of the individual bond areas in the first zone. The second zone comprises a second aggregate bond area, BA2, which is the sum of the individual bond areas in the second zone. In certain embodiments, the second aggregate bond area, BA2 is greater than the first aggregate bond area as shown for example in FIG. 4. The second aggregate bond area can be from about 5% to about 40% greater, or from about 10% to about 20% greater than the first aggregate bond area, reciting for each range every 5% increment therein. In one nonlimiting example, the first zone and the second zone comprise substantially continuous bonds 430 having different areas as shown in FIG. 3. In such nonlimiting example, the bonds 42a, 42b may comprise different lateral widths from longitudinal edge to longitudinal edge. Additionally, or alternatively, the bonds 42a, 42b may comprise different longitudinal lengths. By varying the aggregate bond area between the zones, the cumulative bond integrity can be ensured while minimizing the impact of bonding near the outboard edge 47, which is more likely to closely contact the wearer. Bonding material and/or bond sites often adversely impact softness and flexibility and can cause excess tack or roughness. Consequently, it is desirable to minimize the bonding in the zone that contacts the wearer. Moreover, waist gasketing elements often began to peel from a chassis along an inboard corner. Thus, having more bonding inboard will improve adherence.

Further to the above, the first zone may comprise a first aggregate bond strength and the second zone comprises a second aggregate bond strength. In some embodiments, the second aggregate bond strength is greater than the first aggregate bond strength. In some nonlimiting examples, the Bond Strength Ratio is at least about 1.3, or at least about 1.4, or about least about 1.5, or at least about 1.7, or from about 1.3 to about 3, or from about 1.4 to about 2.5, reciting for each range 0.1 increment therein, as determined by the Bond Strength Test Method. The difference in bond strength may be formed by, for example, different bonding materials, different amounts of bonding materials, the number of bonds in a given area, and/or relative bond areas.

In certain embodiments, the first zone 410 comprises a first total basis weight and the second zone comprises a second total basis weight. The total basis weight is the basis weight of the entire waist gasketing element in said zone, including the waist gasketing element material and bonding materials. The total basis weight can be determined by cutting the zone from the article, measuring the area of the zone, weighing the zone, and dividing the weight by the area. The second total basis weight may be greater than the first total basis weight. This can be achieved, for example, by a greater amount of bonding material, such as adhesive, in the second zone. In nonlimiting examples, the second total basis weight is from about 20% to about 60% greater, or from about 30% to about 50% greater than the first total basis weight, for each range reciting every 5% increment therein.

While the invention is described with respect to two zones for ease of understanding, it is also contemplated and within the scope of the invention that more than two zones be present within a chassis attachment region. Further, without wishing to be bound by theory, the optimal chassis attachment region dimensions (including zone dimensions and number of zones) will vary based on number of considerations, including but not limited to the component materials of layers to be bonded, process conditions including but not limited to line speed and converting operations such as cutting near or on the waist gasketing elements, the bonding technique including but not limited to bonding material and add-on levels, the dimensions of the waist gasketing element and/or chassis, the layer of the chassis to which the waist gasketing element is attached, and materials (such as elastic members) which are included in the waist gasketing element. A sufficient amount of bonding is necessary to ensure adherence and prevent against adhesive creep.

Chassis attachment bonds 42 may be utilized to attach the waist gasketing element to the topsheet, backsheet and/or leg gasketing system. The top and/or the bottom layer 44, 45 may be attached to the topsheet, backsheet and/or leg gasketing system. In embodiments that include a waist gasketing element 40 that has a folded edge 49, a waist gasketing element first material edge 440, and a waist gasketing element second material edge 450, at least a portion of the web of material between the waist gasketing element folded edge 49 and waist gasketing element second material edge 450 may be attached to the web of material forming the leg gasketing system 70. The attachment of the waist gasketing element 40 to the web of material forming the leg gasketing system 70 may be along the longitudinal edge(s) 424 of the first zone and/or the longitudinal edge(s) 425 of the second zone. As seen in the embodiment of FIG. 1, the longitudinal edges 424, 425 may attach at least a portion of the waist gasketing element's web of material between the waist gasketing element folded edge 49 and the waist gasketing element second material edge 450 to the web of material forming the leg gasketing system 70. The longitudinal edges 424, 425 can be located adjacent to the longitudinal edges 48 of the waist gasketing element 40 (or may be coterminous therewith). In another embodiment, the longitudinal edges 424, 425 are located adjacent to an inner cuff folded edge 72 of the leg gasketing system 70 (or may be coterminous therewith). The waist gasketing element 40 may be attached to the leg gasketing system 70 over substantially the entire area that the leg gasketing system 70 overlaps with the waist gasketing element 40. In some embodiments, the waist gasketing element 40 is attached to the leg gasketing system 70 over more than about 50%, more than about 60%, more than about 70%, more than about 80%, more than about 90%, or more than about 95%, of the entire area that the leg gasketing system 70 overlaps with the waist gasketing element 40.

In an embodiment, the waist gasketing element 40 comprises a waist gasketing element pocket 50. The pocket 50 may be formed from a portion of the waist gasketing element 40 that is unattached from the chassis 20 (see FIG. 2 for example).

The waist gasketing element 40 may further comprise one or more laterally extending elastic members 55. In some embodiments, the elastic members may be positioned between i) the portion of the web of material between a waist gasketing element folded edge 49 and the waist gasketing element first material edge 440, and ii) the portion of the web material between the waist gasketing element folded edge 49 and the waist gasketing element second material edge 450.

The elastic members 55 may be elastomeric fibers, such as LYCRA® fibers available from INVISTA of Wichita, KS, in various decitex levels. The skilled person may select the appropriate decitex based on the desired contraction and other principles discussed herein. Other suitable elastics can be made from natural rubber, such as elastic tape sold under the trademark Fulflex 9411 by Fulflex Company of Middletown, R.I. The elastic members 55 may also comprise any heat shrinkable elastic material as is well known in the art. In addition, elastic members 55 may take a multitude of configurations. For example, the width may be varied; a single strand or several parallel or non-parallel strands of elastic material may be used; or a variety of shapes may be used including rectilinear and curvilinear; or a variety of cross sectional shapes can be used (circular, rectangular, square, etc.).

The waist gasketing element 40 may comprise at least two waist elastic members 55, at least three waist elastic members 55, at least four elastic members 55, at least five elastic members 55, at least six waist elastic members 55, at least seven waist elastic members 55, at least eight waist elastic members 55, at least nine waist elastic members 55, at least ten waist elastic members 55, at least eleven waist elastic members 55, or at least twelve waist elastic members 55.

In one embodiment, adjacent elastic members 55 are spaced a longitudinal distance of at least 3.5 mm apart from one edge of the member to the other edge of the member, optionally at least 4 mm apart; optionally at least 4.5 mm apart; optionally at least 5 mm apart; optionally at least 5.5 mm apart; optionally at least 6 mm apart; optionally at least 6.5 mm apart; optionally at least 7 mm apart; optionally at least 7.5 mm apart; optionally at least 8 mm apart; optionally at least 8.5 mm apart; optionally at least 9 mm apart; optionally at least 9.5 mm apart; optionally at least 10 mm apart; optionally at least 10.5 mm apart; optionally at least 11 mm apart; optionally at least 11.5 mm apart; optionally at least 12 mm apart. The spacing between elastic members may be the same or different across the longitudinal length of the waist gasketing element. For example, the spacing between adjacent elastic members could uniformly be 7 mm or there could be variable spacing (i.e., two adjacent elastic members are separated by 3 mm, another two are separated by 6.5 mm, etc.).

In an embodiment, the waist gasketing element 40 may comprise N-fiber. Exemplary N-fiber material is disclosed in U.S. Pat. App. Nos. 62/134,622; 62/186,727.

Figure 5:
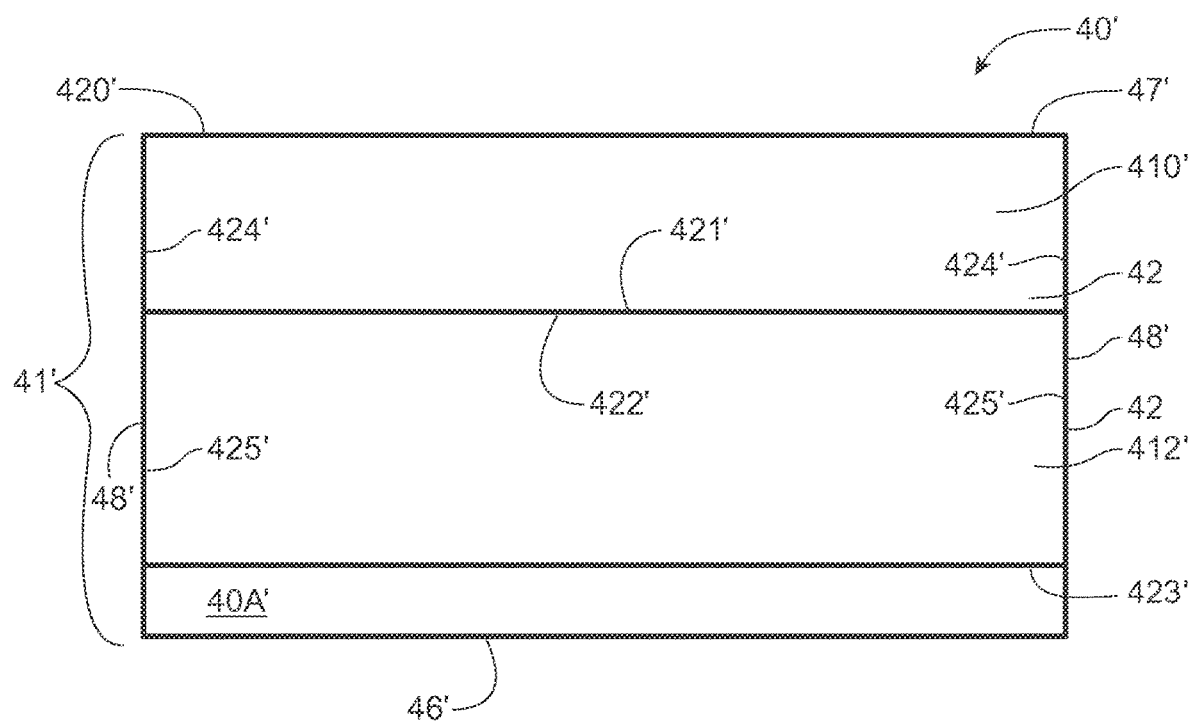
FIG. 5 is a schematic plan view of an exemplary embodiment of a waist gasketing element as detailed herein. The waist gasketing element is shown in a flat, uncontracted state.

Turning to FIG. 5, an article 10 may further comprise a second waist gasketing element 40'. (FIG. 5 is a schematic plan view of a surface 40A' of second waist gasketing element that would be attached to the chassis and/or to the leg gasketing system.) The second waist gasketing element 40' may comprise any of the features described herein with respect to the waist gasketing element 40 (also referred to going forward as the first waist gasketing element 40). By way of nonlimiting example, the second waist gasketing element 40' comprises an inboard lateral edge 46', outboard lateral edge 47', and longitudinal side edges 48'. Similar to the first waist gasketing element, the second waist gasketing element may be formed from a single web of material or multiple webs of materials. Like the first waist gasketing element, the outboard lateral edge 47' of the second waist gasketing element may be coterminous with a waist edge 13, 19 or may be set apart by a longitudinal distance from the waist edge.

The second waist gasketing element 40' may comprise a second chassis attachment region 41', comprising at least two zones 410', 412'. The zones may be adjacent as shown in FIG. 5 or separated by a longitudinal distance. The zones in the second chassis attachment region may comprise bonds 42 formed by different bonding techniques. In nonlimiting examples, the zones comprise different aggregate bond areas, different aggregate bond strengths, and/or different basis weights. The inboard zone 412' may comprise a greater aggregate bond area, greater aggregate bond strength and/or greater basis weight than the outboard zone 410'. The outboard zone 410' may comprise the same bonding technique(s) as the first zone 410 of the first waist gasketing element 40. In some embodiments, the outboard zone 410' comprises the same aggregate bond area, aggregate bond strength, and/or basis weight as the first zone 410 of the first waist gasketing element 40. Alternatively, the outboard zone 410' of the second waist gasketing element may differ from the first zone 410 by bonding technique(s), including for example aggregate bond area, and aggregate bond strength and/or basis weight. Similarly, the inboard zone 412' may be the same as or differ from the second zone 412 of the first waist gasketing element in terms of bonding technique(s). The outboard zone 410' may comprise an outboard bond edge 420' which may be at least partially coextensive with the outboard lateral edge 47' or may be spaced apart from the outboard lateral edge 47'. Likewise, the remaining edges 421', 422', 423', 424', 425' may comprise any of the features described above with respect to edges 421, 422, 423, 424, 425 respectively.

Similar to the first waist gasketing element, the second waist gasketing element may comprise one or more laterally-extending elastic members 55, having any of features described above with respect to elastic members.

Figure 6:
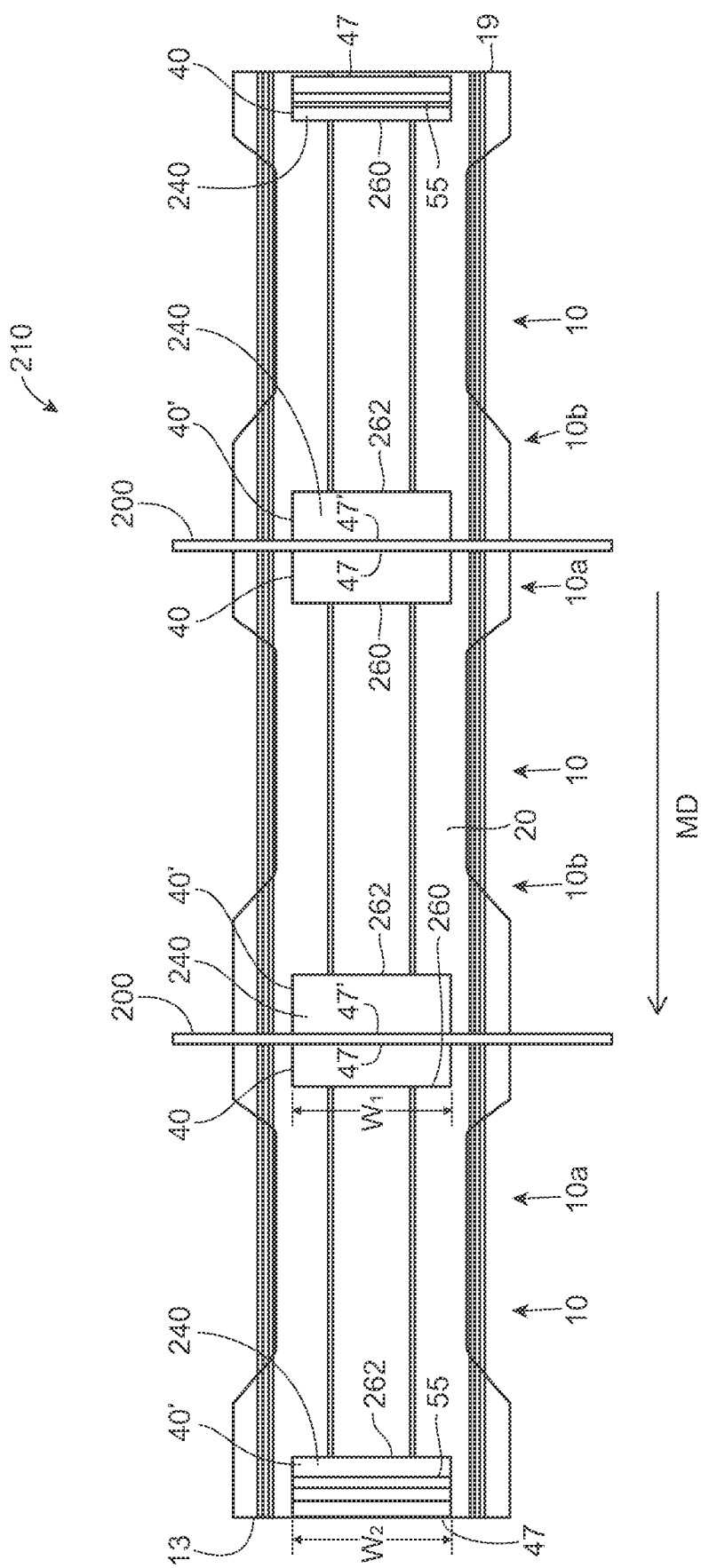
FIG. 6 is a schematic plan view of an exemplary embodiment of a web of multiple absorbent articles.

In an embodiment, the outboard lateral edge 47 of the first waist gasketing element 40 comprises a first width, W1, and the outboard lateral edge 47' of second waist gasketing element comprises a second width, W2. In one nonlimiting example, the first and second widths are the same as shown in FIG. 6. (FIG. 6 is a schematic representation of a web of articles and a separating apparatus.) Alternatively, the first and second widths may be different.

In some embodiments, bonds described herein may include colors or pigments. The colors and/or pigments may be visible through the topsheet and/or visible through the backsheet. Patterns and/or intermittent bonding may be formed through patterned slot coating techniques as taught in U.S. Pat. Pub. Nos. 2014/0148323, 2014/0148773, 2014/0148774 and 2014/0144579 in some embodiments.

A strip of articles 210 comprising waist gasketing elements 40 may be formed by joining multiple waist gasketing elements 240 to a web of chassis material 20 as shown in FIG. 6. Each waist gasketing element 240 in the strip 210 may comprise a first transverse edge 260 and a second transverse edge 262. In embodiments where a waist gasketing element is formed by a single web of material, said web of material may be folded to form the top and bottom layers.

Figure 7:
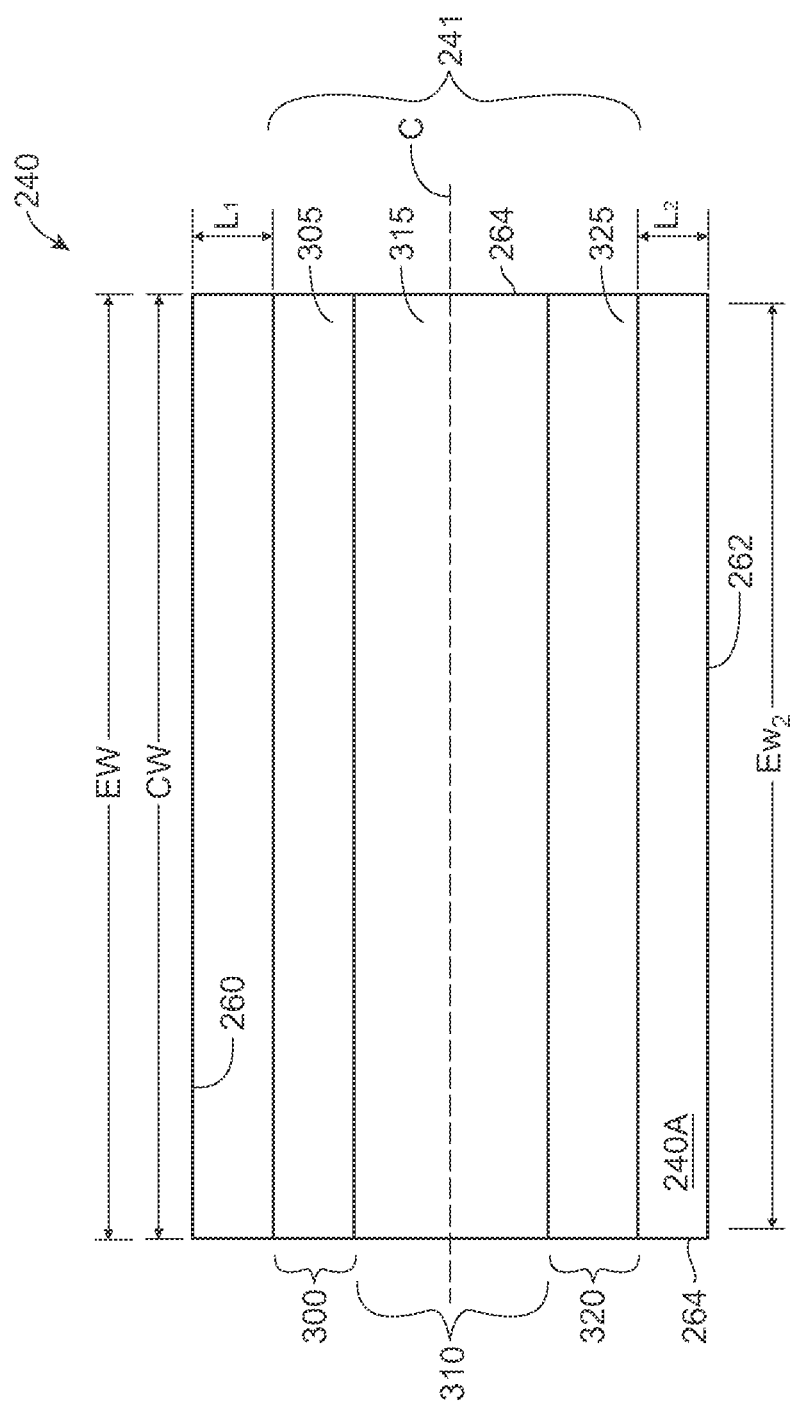
FIG. 7 is a schematic plan view of an exemplary embodiment of a waist gasketing element as detailed herein. The waist gasketing element is shown in a flat, uncontracted state.

Each waist gasketing element 240 may further be provided with a chassis attachment region 241 as shown in FIG. 7. (FIG. 7 is a schematic plan view of the surface 240A of a waist gasketing element that would be attached to the web of chassis material.) The chassis attachment region 241 may comprise a first edge zone 300, a central zone 310, and a second edge zone 320, each having one or more chassis attachment bonds 42. In one nonlimiting example, adhesive is applied to the chassis attachment region 241 in each of the zones 300, 310, 320. Adhesive may be applied at a higher add-on rate in the first edge zone than in the central zone. Additionally, or alternatively, adhesive may be applied at a higher add-on rate in the second edge zone than in the central zone. In a further nonlimiting example, the add-on rate in an edge zone 300, 320 is from about 20% to about 60%, or about 30% to about 50% greater than the add-on rate in the central zone, reciting for each range every 5% increment therein. In some nonlimiting examples, adhesive is applied in a substantially continuous bar. In further nonlimiting examples, adhesive is applied such that a bond comprises open areas 432. Adhesive may be applied by any known method including but not limited to slot coating, patterned slot coating techniques as taught in U.S. Pat. Pub. Nos. 2014/0148323, 2014/0148773, 2014/0148774 and 2014/0144579, spraying and combinations thereof. In nonlimiting examples, the adhesive is applied by slot coating. Applying adhesive to the waist gasketing element provides greater flexibility during manufacturing; all adhesive will be fully utilized without precise aim as opposed to applying the adhesive to the chassis prior to attachment. When applying adhesive to the chassis material, greater effort must be exerted to ensure the adhesive is applied in the area that will subsequently be attached to the waist gasketing element. However, it is also within the scope of the invention that adhesive may be applied to the areas of the chassis material 20 corresponding to the zones 300, 310, 320 rather than being applied directly to the waist gasketing element. In some embodiments, adhesive is applied to both the chassis 20 and the waist gasketing element 240.

In a further embodiment, a first edge bonding technique 305 is applied to the first edge zone 300 and a central bonding technique 315 is applied to the central zone 310. The central bonding technique 315 may differ from the first edge bonding technique 305. In particular, the central and first edge bonding techniques may differ by the type of bonding material, amount of bonding material, bonding method, number of bonds, and/or aggregate bond area. The differences in the bonding techniques may result in different bond strengths and/or basis weights in the zones.

A second edge bonding technique 325 may be applied to the second edge zone 320. The second edge bonding technique 325 may be the same as or may differ from the first edge bonding technique 305. In embodiments, the second edge bonding technique 325 differs from the central bonding technique. In particular, the bonding techniques may differ by the type of bonding material, amount of bonding material, bonding method, number of bonds, and/or aggregate bond area. The differences in the bonding techniques may result in different bond strengths and/or basis weights in the zones.

The waist gasketing elements may be disposed apart from one another by a longitudinal distance in the machine direction and joined to the chassis material at the chassis attachment regions. As schematically shown in FIG. 6, a separating apparatus 200 (such as a knife) may be used to separate the strip 210 into individual articles 10. The separating apparatus 200 may cut the strip 210 laterally between the transverse edges 260, 262 of the waist gasketing elements. The separating apparatus 200 may be programmed or otherwise directed to cut at target zones on the strip of articles. However, given manufacturing viabilities, the separating apparatus 200 may not be able to consistently hit the targets. The chassis attachment region may cover a longitudinal distance and/or lateral distance that encompasses and extends beyond the target zone. In particular, the central zone may cover a longitudinal distance that encompasses and extends beyond the target zone as can be seen in FIG. 7 for example, where the cut is depicted by C. In some embodiments, the central zone is from about 10 mm to about 35 mm, or about 25 mm in the longitudinal direction (i.e., length), reciting for said range every 5 mm increment therein. The strip may be cut within the central zone such that the central zone becomes an article's first zone 410 as described above, and the edge zone 300 or 320 becomes the second zone 412 as described above. Further, the strip may be cut such that the resultant first zone comprises a longitudinal length that is less than the length of the edge zone (i.e., less than the resultant second zone's length).

The central zone may further comprise a transverse width, CW, which is the greatest lateral distance between bond edges in central zone. Where the central zone comprises more than one chassis attachment bond, the width may be measured between edges of different bonds 42. In some embodiments, the central zone is at least partially coextensive with a longitudinal edge 264 of the waist gasketing element. In one nonlimiting example, the central zone is at least partially coextensive with both longitudinal edges 264. Alternatively, the central zone may not extend to transverse edges 264.

The first edge zone may be at least partially coextensive with the first transverse edge 260 or be separated by a longitudinal distance, $L_1$, from the transverse edge. In some embodiments, $L_1$ can be from about 0 mm to about 4 mm. Likewise, the second edge zone may be at least partially coextensive with the second transverse edge or separated by a longitudinal distance, $L_2$, from the second transverse edge. $L_2$ may be the same as or may differ from $L_1$. In some embodiments, $L_2$ can be from about 0 mm to about 4 mm. The first and/or the second edge zone may comprise respective longitudinal lengths that are less than the longitudinal length of the central zone. Alternatively, the first and/or second edge zone may comprise respective longitudinal lengths that are greater than or equal to the longitudinal length of the central zone. The first and second edge zone may comprises the same or different lengths. In further embodiments, the first edge zone comprises a first edge width, EW, which is the greatest lateral distance between bond edges in the first edge zone. The first edge width, EW, may be the same as the central zone width, CW, as shown in FIG. 7. Alternatively, the first edge width, EW, may be greater than or less than the central zone width. Likewise, the second edge zone may comprise a second edge width, $EW_2$, which is the greatest lateral distance between bond edges in the second edge zone. The second edge width, $EW_2$, may be the same as the first edge width, EW, and/or as the central zone width, CW. Alternatively, the second edge width, $EW_2$, may be less than or may be greater than the first edge width, EW, and/or the central zone width, CW.

Each cut results in a leading article 10a and a trailing article 10b. The cut forms the back waist edge 19 of the leading article 10a and the front waist edge 13 of the trailing article 10b. The cut may form the outboard lateral edge of a waist gasketing element 40 disposed in the second waist region of the leading article and/or form the outboard lateral edge of a waist gasketing element 40' disposed in the first waist region of the trailing article. The cut may further result in two waist gasketing elements 40, each on separate articles 10, which have outboard zones 410 comprising less bonding, less basis weight and/or lower bond strength than inboard zones 412. In this way, the edge of the waist gasketing elements are softer and flexible while the inboard zone ensures the waist gasketing element remains fixed on the article. The resulting two waist gasketing elements can have the same dimensions or different dimensions (e.g., length, width, area). In this way, a front waistband can comprise different dimensions than a rear waistband.

Leg Gasketing System

The absorbent article 10 may comprise a leg gasketing system 70 attached to the chassis 20. The leg gasketing system 70 comprises one or more cuffs 71. The leg gasketing system 70 may be constructed as, and comprise one or more features, disclosed in commonly assigned U.S. App. Nos. 62/134,622; 62/186,727.

FIGS. 8a and 8b depict schematic cross sectional views of the exemplary leg gasketing systems of FIG. 1 in a flat, uncontracted state, the views taken through the lateral centerline 110 (FIG. 8a is a schematic cross section of the left leg gasketing system, and FIG. 8b is a schematic cross section of both leg gasketing systems in relation to the topsheet).

In an embodiment, the leg gasketing system 70 comprises an inner cuff 72 having an inner cuff edge 73. The inner cuff edge 73 may comprise an inner cuff material edge 74. Alternatively, the inner cuff material edge 74 may be folded such that the cuff edge 73 comprises a folded inner cuff edge 75. The leg gasketing system 70 may further comprise an outer cuff 76 that comprises an outer cuff edge 77. The outer cuff edge 77 may comprise the outer cuff material edge 78. Alternatively, the outer cuff material edge 78 may be folded such that the outer cuff edge 77 comprises a folded outer cuff edge 79.

In one embodiment, each leg gasketing system 70 comprises a single, continuous web of material. In other embodiments, the leg gasketing system 70 may be formed from more than one web of material (e.g., multiple webs of material that are joined together to become one web of material, or multiple distinct webs of material that are separate from the disposable absorbent article chassis and form part of the leg gasketing system). Herein, locations (e.g., folded edge, material edge, etc.) on the leg gasketing system 70 are detailed in reference to "a web of material" or "a portion of the web of material." The recitations of "a web of material" or "the web of material" refer to leg gasketing system embodiments that may be formed from a single, continuous web of material, multiple webs of material that are joined together to become one web of material, or multiple distinct webs of material that are separate from the disposable absorbent article chassis and form part of the leg gasketing system. All such embodiments are contemplated.

In some embodiments, the web of material is folded laterally inward (toward the longitudinal centerline 100 of the absorbent article 10) to form the outer cuff folded edge 79 and folded laterally outward (away from the longitudinal centerline 100 of the absorbent article 10) to form the inner cuff folded edge 75.

The cuffs 71 may be attached to the chassis 20 and/or each other 72, 76 by any suitable means. In an embodiment, the outer cuff 76 is attached to the chassis 20 through one or more cuff attachment bonds 82 as illustrated in FIG. 8b. Further, a cuff attachment bond 82 may attach at least portion of web material in the outer cuff 76 to the opacity strengthening patch 80 in at least a portion of the first waist region 14 and at least a portion of the second waist region 18 (not shown).

In an embodiment, the inner cuff edge 73 comprises a folded edge 75 and the outer cuff edge 77 comprises a folded outer cuff edge 79. In such embodiment, at least a portion of the web material between the inner cuff folded edge 75 and the outer cuff folded edge 79 can be attached to at least a portion of the web of material between the outer cuff folded edge 79 and the outer cuff material edge 78 in at least the crotch region 16 and the first waist region 14. The attachment of the web of material between the inner cuff folded edge 75 and the outer cuff folded edge 79 to the web of material between the outer cuff folded edge 79 and the outer cuff material edge 78 in at least the crotch region 16 and the first waist region 14 is made through utilization of one or more cuff separation bonds 84. The leg gasketing system 70 may further comprise a pocket 85 arising from the web of material between the inner cuff folded edge 75 and the outer cuff folded edge 79 being unattached to the web of material between the outer cuff folded edge 79 and the outer cuff material edge 78 in one of the waist regions 14, 18 as shown in FIG. 8b. The pocket 85 may provide additional void volume within the leg gasketing system 70 to receive exudates to help isolate fecal material from the wearer's skin as well as contain exudates between the layers of the leg gasketing system 70 to prevent leakage. The pocket 85 may comprise an opening created by a break in the cuff separation bond 84 or a series of breaks in the cuff separation bond 84. The pocket and opening can occur in the first waist region 14, the second waist region 18 or the crotch region 16 as needed for the specific type of exudates and particular situation where leakage prevention is desired. Attachment of the outer cuff 76, the opacity patch 80 and/or inner cuff 72 and/or formation of the pocket 85 may be accomplished in accordance with the disclosure of commonly assigned U.S. patent App. No. 62/134,622. The leg gasketing system 70 may comprise one or more longitudinally extending elastic members 55 as can be seen in FIG. 1. The pocket 85 may be free from elastics 55.

Opacity Strengthening Patch

In some embodiments of the disposable absorbent articles detailed herein, an opacity strengthening patch 80 may be included as part of the chassis 20. The opacity strengthening patch 80 is an additional layer of material. The opacity strengthening patch 80 may be connected to the leg gasketing system 70, the polymeric film layer, and/or the backsheet 26. The opacity strengthening patch 80 may be disposed between the backsheet 26 and leg gasketing system 70 in either the first waist region 14, the second waist region 18, or both the first waist region 14 and the second waist region 18 of the article; the opacity strengthening patch 80 may overlap at least one of the leg gasketing system 70 and/or the polymeric film layer (i.e., inner layer of the backsheet 26). The opacity strengthening patch 80 may be attached to one or both of the leg gasketing system 70 or the polymer film layer using any suitable means such as glue, mechanical bonds, thermal bonds, or the like, so that loads generated during the application process or during wear can be transferred from the lateral edge of the article to the leg gasketing system 70 and/or the polymeric film layer. The opacity strengthening patch is useful in providing the strength needed to prevent the article from extending excessively during application and wearing; it also may provide opacity at the sides and waist to prevent the skin of the user from showing through the article. Thus, the patch 80 may be located at any portion of the chassis 20 where strength and opacity is desirable. Suitable opacity strengthening patches are disclosed in U.S. Pat. App. Nos. 62/134,622; 62/186,727.

Construction Materials

It is recognized that there are many combinations of material lateral tensile properties that could form a substantially suitable force transmission pathway in the waist region or the article without excessive lateral stretch in the waist region, and that the material force pathways may go from the opacity strengthening patch directly into the polymeric film layer or into the polymeric film layer through a variety of other layers in the region immediately outboard the polymeric film layer. These layers may include the topsheet, backsheet nonwoven, cuff, absorbent assembly, leg gasketing system, or any other layer that is located in a region adjacent to the polymeric film layer.

In one embodiment, the material of the leg gasketing system 70 is made from a substantially liquid impervious material. The material may be selected from the group consisting of an SMS nonwoven, SMMS nonwoven material, or a nonwoven component layer comprising "N-fibers".

Various nonwoven fabric webs may comprise spunbond, meltblown, spunbond ("SMS") webs comprising outer layers of spunbond thermoplastics (e.g., polyolefins) and an interior layer of meltblown thermoplastics. In one embodiment of the present invention, the leg gasketing cuff 70 comprises a nonwoven component layer having fine fibers ("N-fibers") with an average diameter of less than 1 micron (an "N-fiber layer") may be added to, or otherwise incorporated with, other nonwoven component layers to form a nonwoven web of material. In some embodiments, the N-fiber layer may be used to produce a SNS nonwoven web or SMNS nonwoven web, for example. Suitable construction materials, including N-fibers, are disclosed in U.S. Pat. App. No. 62/134,622; 62/186,727.

Package

The absorbent articles 10 of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 9:
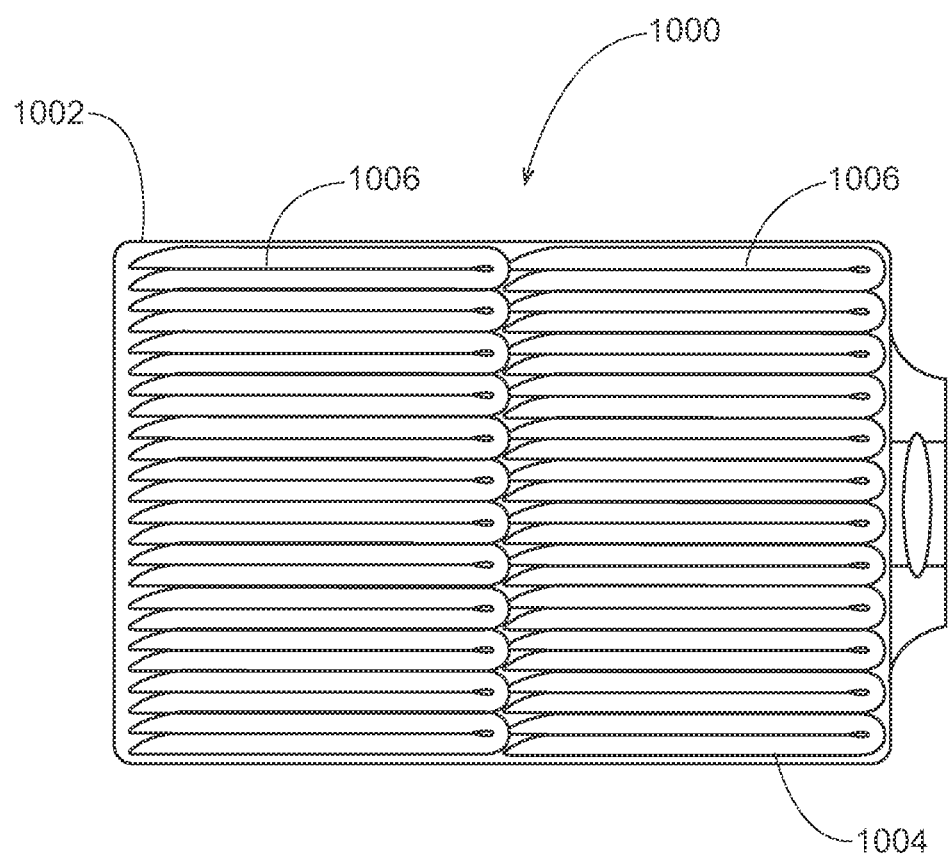
FIG. 9 is a schematic side elevation view of a package in accordance with one embodiment of the present invention.

FIG. 9 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

COMBINATION OF EMBODIMENTS

While embodiments are described separately herein for brevity and clarity, combinations of the various embodiments are contemplated and within the scope of the present disclosure.

A. An absorbent article for wearing about the lower torso of a wearer, the absorbent article comprising:
a first waist region having a first waist edge, a second waist region having a second waist edge, a crotch region disposed between the first and second waist regions; and a first longitudinal edge and a second longitudinal edge;
a chassis comprising a topsheet, a backsheet, and an absorbent core disposed between the topsheet and backsheet; and
a waist gasketing element having an inboard lateral edge and an outboard lateral edge, the waist gasketing element being disposed in one of the first or the second waist regions and joined to the chassis in a chassis attachment region,
wherein:
the chassis attachment region comprises a first zone proximate to the outboard lateral edge and a second zone disposed longitudinally inboard of the first zone,
each of the first and the second zones comprise one or more chassis attachment bonds; and
the first zone differs from the second zone by bonding technique, aggregate bond strength and/or total basis weight.

B. The absorbent article of paragraph 1 wherein the first zone comprises a first aggregate bond area and the second zone comprises a second aggregate bond area, wherein the second aggregate bond area is greater than the first aggregate bond area, in particular wherein the second aggregate bond area is from about 10% to about 20% greater than the first aggregate bond area.

C. The absorbent article of paragraphs 1 or 2 wherein the first zone comprises a first aggregate bond strength and the second zone comprises a second aggregate bond strength, wherein the second aggregate bond strength is greater than the first aggregate bond strength.

D. The absorbent article of any of the preceding paragraphs wherein the first zone comprises a first total basis weight and the second zone comprises a second total basis weight, wherein the second total basis weight is greater than the first total basis weight, in particular wherein the second total basis weight is from about 30% to about 50% greater than the first total basis weight.

E. The absorbent article of any of the preceding claims, wherein the outboard lateral edge is at least partially coextensive with the waist edge of the one of the first or the second waist regions.

F. The absorbent article of any of the preceding paragraphs wherein the first zone comprises an adhesive chassis attachment bond.

G. The absorbent article of paragraph F wherein the adhesive chassis attachment bond is in the form of a first continuous bar.

H. The absorbent article of paragraph F wherein the adhesive chassis attachment bond comprises one or more open areas.

I. The absorbent article of any of the preceding paragraphs wherein the second zone comprises a second adhesive chassis attachment bond.

J. The absorbent article of paragraph I wherein the second adhesive chassis attachment bond is in the form of a second continuous bar.

K. The absorbent article of paragraph I wherein the second adhesive chassis attachment bond comprises a web-like structure having one or more open areas.

L. The absorbent article of any of the preceding paragraphs wherein the first zone comprises an outboard bond edge that is at least partially coextensive with the waist edge.

M. The absorbent article of any of the preceding paragraphs wherein the waist gasketing element is disposed on the body-facing side of the chassis.

N. The absorbent article of any of the preceding paragraphs wherein the waist gasketing element is at least partially disposed on the topsheet.

O. The absorbent article of any of the paragraphs A-L wherein the waist gasketing element is at least partially disposed on the garment-facing side of the chassis.

P. The absorbent article of any of the preceding paragraphs wherein the waist gasketing element is at least partially disposed on the leg gasketing system.

Q. The absorbent article of any of the preceding paragraphs further comprising a second waist gasketing element disposed in the other of the first or second waist regions, in particular wherein the second waist gasketing element comprises a second chassis attachment region having two or more zones wherein at least two of the two or more zones comprise different bonding techniques, aggregate bond strengths and/or total basis weights.

R. The absorbent article of any of the preceding paragraphs wherein the chassis attachment bonds of the first zone are formed by a different bonding technique than the chassis attachment bonds of the second zone, in particular where the different bonding techniques comprise a different combination of bonding materials.

S. A method of forming a waist gasketing element of any of the preceding paragraphs comprising the steps of:
providing a web of chassis material;
providing a plurality of waist gasketing elements, each waist gasketing element having a first transverse edge and a second transverse edge;
applying an adhesive on each waist gasketing element in a chassis attachment region comprising a central zone and two edge zones, and applying a greater amount of adhesive in at least one of the edge zones than in the central zone, in particular 30-50% more;
joining the waist gasketing elements to the web of chassis material at the chassis attachment regions and thereby forming a strip of final articles;
dividing the strip of final articles between the first and second transverse edges of the waist gasketing elements such that a cut separates two final articles, the two final articles comprising a leading article and a trailing article, wherein each cut:
is disposed at least partially within the central zone;
forms a back waist edge of the leading article and a front waist edge of the trailing article; and
forms an outboard lateral edge of a back waist gasketing element on the leading article and an outboard lateral edge of a front waist gasketing element on the trailing article.

T. A method of forming the absorbent article of any of paragraphs A-R comprising the steps of:
providing a web of chassis material;
providing a plurality of waist gasketing elements, each waist gasketing element having a first transverse edge and a second transverse edge;
providing a chassis attachment region on each waist gasketing element, the chassis attachment region comprising a central zone and a first edge zone and a second edge zone;
applying a central bonding technique to the central zone and a first edge bonding technique to the first edge zone, wherein the central and first edge bonding techniques are different;
joining the waist gasketing elements to the web of chassis material at the chassis attachment regions and thereby forming a strip of final articles;
dividing the strip of final articles between the first and second transverse edges of the waist gasketing elements such that a cut separates two final articles, the two final articles comprising a leading article and a trailing article, wherein each cut:
is disposed at least partially within the central zone;
forms a back waist edge of the leading article and a front waist edge of the trailing article; and
forms an outboard lateral edge of a back waist gasketing element on the leading article and an outboard lateral edge of a front waist gasketing element on the trailing article.

U. The absorbent article of paragraph T wherein the central and first edge bonding techniques differ by one of the group of type of bonding material, amount of bonding material, bonding method, number of bonds, and/or aggregate bond area.

V. The absorbent article of paragraphs T or U further comprising applying a second edge bonding technique to the second edge zone, and wherein said second edge bonding technique is different from the central bonding technique by one of the group of the one bonding material, bonding method, number of bonds, aggregate bond area, and/or aggregate bond strength.

Test Methods

Bond Strength Test

The bond strength of the waist gasketing element and portions thereof is measured on a constant rate of extension tensile tester with computer interface (a suitable instrument is the MTS Insight using Testworks 4.0 Software, as available from MTS Systems Corp., Eden Prairie, MN) using a load cell for which the forces measured are within 1% to 90% of the limit of the cell. Both the movable (upper) and stationary (lower) jaws are fitted with bar grips, wider than the width of the test specimen. All testing is performed in a conditioned room maintained at about 23° C.±2° C. and about 50%±2% relative humidity.

Program the tensile tester to perform a 180 degree peel test. The crosshead is moved at 63.5 mm/min until complete separation of the belt. Force and extension data are collected at a rate of 50 Hz.

Condition the sample articles at about 23° C.±2° C. and about 50%±2% relative humidity for at least two hours before testing. Stretch out and secure the article to a lab bench with the back sheet facing upward. Cut a 2.54 mm wide specimen, through all layers of the article, perpendicular to the waist and centered along the longitudinal centerline of the article. Extend the strip approximately 10 mm longer than the longitudinal length of the waist band. Stretch the specimen strip in the lateral direction to the full 2.54 mm width and secure to the bench with the top sheet facing upward. Gently peel approximately 5 mm of the waist band away from the chassis beginning at the proximal (inboard) edge of the waist band. Prepare ten (10) specimens from ten replicate articles.

Set the gage length to 5.0 mm using a gage block. Zero the cross head. Insert the pre-peeled portion of the waist band into the upper grips, making sure the strip is perpendicular to the width of the grip. The portion of the specimen in the grip is extended laterally to the full 2.54 width. Close the upper grip. Place the chassis end of the specimen into the bottom grips, insuring that the specimen is perpendicular to the grip and eliminating any slack. The portion of the specimen in the grip is extended laterally to the full 2.54 width. Close the bottom grip. Zero the load cell. Start the tensile program and collect data.

Construct force (N) verses extension (mm) curve. Truncate the first 5.0 mm and the last 5.0 mm of the curve. Divide the remaining curve into 3 equal extension segments (mm). Calculate the average force (N) in the first segment (Inboard Edge of the Waist Element) and the third segment (Outboard/Distal Edge of the Waist Element) and record each to the nearest 0.001 N. In like fashion analyze all ten samples and report as the average Inboard Edge Adhesion Strength (N) and Distal Edge Adhesion Strength (N). The Bond Strength Ratio is the average Inboard Edge Adhesion Strength divided by the average Distal Edge Adhesion Strength.

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 9). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for wearing about the lower torso of a wearer, the absorbent article comprising:
a first waist region having a first waist edge, a second waist region having a second waist edge, a crotch region disposed between the first and second waist regions; and a first longitudinal edge and a second longitudinal edge;
a chassis comprising a topsheet, a backsheet, and an absorbent core disposed between the topsheet and backsheet;
a leg gasketing system comprising at least one of an inner cuff and outer cuff;
a waist gasketing element having an inboard lateral edge, an outboard lateral edge, a first longitudinal edge, and an opposing second longitudinal edge, the waist gasketing element being disposed in one of the first waist region and the second waist region;
a first zone proximate to the outboard lateral edge and the first and second longitudinal edges, and a second zone disposed longitudinally inboard of the first zone and adjacent the first and second longitudinal edges and the inboard lateral edge;
wherein the first zone comprises a plurality of intermittent bonds and open areas;
wherein the second zone comprises a plurality of intermittent bonds and open areas;
wherein the first zone comprises a first aggregate bond area and the second zone comprises a second aggregate bond area, wherein the second aggregate bond area is not equal to the first aggregate bond area;
wherein the waist gasketing element is bonded with the topsheet with the plurality of intermittent bonds in the second zone; and
wherein the waist gasketing element is bonded with the leg gasketing system with the plurality of intermittent bonds in the first zone.

2. The absorbent article of claim 1, wherein the outboard lateral edge is at least partially coextensive with the waist edge of the one of the first or the second waist regions.

3. The absorbent article of claim 2, wherein the first zone comprises an outboard bond edge that is at least partially coextensive with the waist edge of the one of the first and second waist regions.

4. The absorbent article of claim 1, wherein at least one of the inboard lateral edge and the outboard lateral edge comprises a folded edge.

5. The absorbent article of claim 1, wherein the waist gasketing element comprises an elastomeric film.

6. The absorbent article of claim 1, wherein the waist gasketing element is at least partially disposed on the body-facing side of the chassis.

7. The absorbent article of claim 1, wherein the waist gasketing element is at least partially disposed on the garment-facing side of the chassis.

8. The absorbent article of claim 1, wherein the second aggregate bond area is from about 10% to about 20% greater than the first aggregate bond area.

9. The absorbent article of claim 1, wherein the first zone comprises a first aggregate bond strength and the second zone comprises a second aggregate bond strength, wherein the second aggregate bond strength is different than the first aggregate bond strength.

10. The absorbent article of claim 9, wherein the waist gasketing element comprises a Bond Strength Ratio of at least 1.4.

11. The absorbent article of claim 1, wherein the plurality of intermittent bonds of the first zone and the plurality of intermittent bonds of the second zone are formed by different bonding techniques.

12. The absorbent article of claim 11, wherein the different bonding techniques comprise at least one of adhesive bonding, ultrasonic bonding, pressure bonding, and heat bonding.

13. The absorbent article of claim 11, wherein the first zone comprises a first total basis weight and the second zone comprises a second total basis weight, wherein the second total basis weight is different than the first total basis weight.

14. The absorbent article of claim 13, wherein the second total basis weight is from about 30% to about 50% greater than the first total basis weight.

15. The absorbent article of claim 13, further comprising a second waist gasketing element disposed in the other of the first or second waist regions, wherein the second waist gasketing element comprises two or more attachment zones, and wherein at least two of the attachment zones comprise different basis weights.

16. The absorbent article of claim 1, wherein the waist gasketing element comprises elastomeric strands.

17. The absorbent article of claim 1, wherein the absorbent article is a pant-type diaper having pre-formed waist opening and leg openings.

18. The absorbent article of claim 17, wherein the pant-type diaper is refastenable.

* * * * *